(12) United States Patent
Sawant et al.

(10) Patent No.: US 9,180,384 B2
(45) Date of Patent: Nov. 10, 2015

(54) APPARATUS AND PROCESS FOR USING OLEFIN AS AN AZEOTROPIC ENTRAINER FOR ISOLATING 1,3-DICHLORO-2-PROPANOL FROM A 2,2'-OXYBIS (1-CHLOROPROPANE) WASTE STREAM

(75) Inventors: Mahesh Ratnakar Sawant, Pune, IN (US); Edward D. Daugs, Midland, MI (US); Mark R. Smit, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 330 days.

(21) Appl. No.: 13/990,356

(22) PCT Filed: Dec. 7, 2011

(86) PCT No.: PCT/US2011/063697
§ 371 (c)(1),
(2), (4) Date: May 29, 2013

(87) PCT Pub. No.: WO2012/078728
PCT Pub. Date: Jun. 14, 2012

(65) Prior Publication Data
US 2013/0253229 A1    Sep. 26, 2013

Related U.S. Application Data

(60) Provisional application No. 61/421,910, filed on Dec. 10, 2010.

(51) Int. Cl.
| | |
|---|---|
| *C07C 29/80* | (2006.01) |
| *C07C 29/86* | (2006.01) |
| *C07C 29/74* | (2006.01) |
| *C07C 29/78* | (2006.01) |
| *B01D 3/36* | (2006.01) |
| *C07C 29/82* | (2006.01) |

(52) U.S. Cl.
CPC . *B01D 3/36* (2013.01); *C07C 29/74* (2013.01); *C07C 29/80* (2013.01); *C07C 29/82* (2013.01); *C07C 29/86* (2013.01); *C07C 29/78* (2013.01)

(58) Field of Classification Search
CPC ........ C07C 29/80; C07C 29/86; C07C 29/78; C07C 29/74
USPC .................................................. 568/868, 918
See application file for complete search history.

(56) References Cited

U.S. PATENT DOCUMENTS

| | | | |
|---|---|---|---|
| 1,917,391 A | 7/1933 | Othmer | |
| 2,050,234 A | 8/1936 | Othmer | |
| 4,045,294 A | 8/1977 | Becker et al. | |
| 4,476,336 A | 10/1984 | Sherwin | |
| 4,661,208 A | 4/1987 | Honma et al. | |
| 5,425,853 A | 6/1995 | Berg | |
| 5,928,478 A | 7/1999 | Berg | |
| 2009/0281359 A1 | 11/2009 | Daugs et al. | |
| 2010/0029960 A1 | 2/2010 | Fan et al. | |
| 2010/0298595 A1 | 11/2010 | Matsuda et al. | |

FOREIGN PATENT DOCUMENTS

| | | |
|---|---|---|
| CN | 1596237 A1 | 3/2005 |
| CN | 101712661 | 5/2010 |
| CN | 101805243 | 8/2010 |
| DE | 1210774 | 2/1966 |
| GB | 298137 | 9/1929 |
| GB | 815091 | 6/1959 |
| JP | 2000239201 | 9/2000 |
| JP | 2010047492 | 3/2010 |
| PL | 163256 | 2/1994 |
| PL | 176853 | 6/1994 |
| WO | WO2008128004 | 10/2008 |
| WO | WO2008128010 | 10/2008 |
| WO | WO2009013623 | 1/2009 |
| WO | WO2009126415 | 10/2009 |
| WO | WO2009137282 | 11/2009 |
| WO | WO2010102368 | 9/2010 |
| WO | WO2012078725 | 6/2012 |

OTHER PUBLICATIONS

Chinese Patent Application No. 201180059755.3, Notification of the Second Office Action, mailed Mar. 10, 2015.
International Application No. PCT/US2011/063692, International Search Report, mailed Mar. 2, 2012.
International Application No. PCT/US2011/063692, Written Opinion of the International Searching Authority, mailed Mar. 2, 2012.
International Application No. PCT/US2011/063692, International Preliminary Report on Patentability, mailed Jun. 20, 2013.
International Application No. PCT/US2011/063697, International Search Report, mailed Mar. 13, 2012.
International Application No. PCT/US2011/063697, Written Opinion of the International Searching Authority, mailed Mar. 13, 2012.
International Application No. PCT/US2011/063697, International Preliminary Report on Patentability, mailed Jun. 20, 2013.
Fredenslund et al., Group-Contribution Estimate of Activity Coefficients in Nonideal Liquid Mixtures, AIChE Journal, vol. 21, No. 6, Nov. 1975, pp. 1086-1099.
Chinese Patent Application No. 201180059755.3, Notification of First Office Action, Jun. 20, 2014.
Japanese Patent Application No. 2013-543304, Notice of Reasons for Rejection, mailed Sep. 9, 2014.

*Primary Examiner* — Elvis O Price
(74) *Attorney, Agent, or Firm* — McDonnell Boehnen Hulbert & Berghoff LLP

(57) ABSTRACT

Disclosed are a process and an apparatus for using an olefin as an azeotropic entrainer to isolate a target organic compound from a waste stream. The olefin may be, for example, 1-decene, 1-dodecene, or 1-tetradecene. The target organic compound may be 1,3-dichloro-2-propanol in waste stream comprising a 2,2'-oxybis(1-chloropropane).

11 Claims, 9 Drawing Sheets

APPARATUS AND PROCESS FOR USING OLEFIN AS AN AZEOTROPIC ENTRAINER FOR ISOLATING 1,3-DICHLORO-2-PROPANOL FROM A 2,2'-OXYBIS (1-CHLOROPROPANE) WASTE STREAM

CROSS REFERENCE TO RELATED APPLICATION

The present application claims priority to International Application No. PCT/US11/63697, filed Dec. 7, 2011, which claims priority to U.S. Provisional Patent Application No. 61/421,910 filed on Dec. 10, 2010, all of which are incorporated herein by reference in their entireties.

FIELD

This invention relates to the use of an olefin as an azeotropic entrainer to isolate a target organic compound. More particularly, this invention relates to processes and apparatuses for using an olefin, such as 1-decene, 1-dodecene, or 1-tetradecene, as an azeotropic entrainer to isolate 1,3-dichloro-2-propanol from a waste stream that includes 2,2'-oxybis(1-chloropropane).

BACKGROUND 1,3-dichloro-2-propanol (DCP) is a di-functional raw material that may be useful in various processes. It may be prepared by chlorination of glycerin (K. Kawahata, Y. Awano, Y. Hara, Japanese Patent Publication No. JP2010047492 (2010)), and is an intermediate in the production of epichlorohydrin, useful for the manufacture of epoxy resins, from glycerin (E. Van der Graaf, L. Gonclaves de Mendonca Filho, WO2010102368 (2010); D. Shi, X. Che, Z. Shen, Y. Song, L. Fu, P. Dong, J. Jin, Q. Zhou, B. Gao, Chinese Patent CN101805243 (2010); W. Fan, C. Kneupper, S. Noormann, R. Patrascu, B. Hook, C. Lipp, M. Cloeter, H. Groenewald, United States Patent Application No. 2010/029960 (2010)). As part of the isomeric mixture of 1,3-dichloro-2-propanol and 2,3-dichloro-1-propanol mixture obtained by chlorohydroxylation of allyl chloride with hypochlorous acid, reaction of DCP with base generates epichlorohydrin (M. Spadlo, A. Brzezicki, J. Dula, T. Wilusz, W. Madej, A. Gorzka, E. Okińska, T. Koziel, J. Wasilewski, Polish Patent PL176853 (1999); D. Shi, Y. Song X. Che, P. Dong, B. Gao, Chinese Patent CN101712661 (2010)).

Reaction of epichlorohydrin with hydrogen chloride produces primarily DCP, with a trace of the 2,3-isomer and other by-products (M. Spadlo, M. Adamczyk, A. Brzezicki, J. Dula, K. Giza, A. Gorzka, W. Madej, G. Masztalerz, E. Okińska, Z. Pokorska, M. Stajszczyk, Z. Zawiski, Polish Patent PL163256 (1994); H. Schmidt-Neuhaus, DE1210774 (1966)).

One low cost source of DCP is the distillation residue from a propylene oxide/propylene glycol process. Functionalization of propylene by hydrochlorination to generate propylene oxide and propylene dichloride also generates epichlorohydrin as a by-product. Following recovery of the epichlorohydrin and other products by distillation, a waste stream, often referred to as the Crude PDC Bottoms, remains. Although the accessible amount of epichlorohydrin has been recovered from this waste stream, it still contains residual epichlorohydrin and other by-products.

The residual epichlorohydrin in the Crude PDC Bottoms can be converted to DCP by reacting with hydrogen chloride. However, the isolation and purification of the DCP generated is difficult due to an azeotrope formation of DCP with 2,2'-oxybis(1-chloropropane), one of the major by-products of the propylene oxide/propylene glycol waste stream. An azeotrope is a mixture of two or more liquids in such a ratio that its composition cannot be changed by simple distillation, because when the solution is boiled, the vapor that results has the same ratio of constituents as the original liquid mixture. This may be because the boiling point temperature of the azeotrope is less than the boiling point temperatures of any of its constituents (a positive azeotrope) or because the boiling point temperature of the azeotrope is greater than the boiling point temperatures of any of its constituents (a negative azeotrope). Traditional heterogeneous azeotropic distillation requires an additional column for entrainer recovery. Alternative methods of conventional distillation are time-consuming and costly. A need exists, therefore, for a simplified and economic processes and apparatuses for isolating DCP from the 2,2'-oxybis(1-chloropropane)-containing Crude PDC Bottoms waste stream.

BRIEF SUMMARY

In one aspect, an illustrative embodiment provides a process comprising supplying a feed stream and an olefin stream to a first distillation column, the feed stream comprising a target organic compound; using the olefin as an entrainer in the first distillation column such that the feed stream is separated into at least a first top stream and a first bottom stream; and using a second distillation column to separate the first top stream into at least a second top stream and a second bottom stream. The second bottom stream may comprise the target organic compound and the olefin. The process may further comprise separating the second bottom stream in a separator to produce a third bottom stream and the olefin stream, wherein the third bottom stream comprises the target organic compound. In an alternative embodiment, the process may further comprise reacting the target organic compound in the second bottom stream with the olefin in the second bottom stream.

In another aspect, an illustrative embodiment provides a process for isolating 1,3-dichloro-2-propanol, the process comprising supplying a feed stream which includes 1,3-dichloro-2-propanol and 2,2'-oxybis(1-chloropropane) to a first distillation column, supplying an olefin stream comprising an olefin to the first distillation column, and using the olefin as an entrainer in the first distillation column, such that the first stream is separated into at least a first top stream and a first bottom stream. The first top stream comprises 1,3-dichloro-2-propanol and the olefin and the first bottom stream comprises 2,2'-oxybis(1-chloropropane). The process further comprises supplying the first top stream to a second distillation column and using the second distillation column to separate the first top stream into at least a second top stream and a second bottom stream, wherein the second bottom stream comprises 1,3-dichloro-2-propanol and the olefin, and the second top stream comprises lighter boiling impurities carried into the second column from the first top stream. The second bottoms stream is separated in a separator into at least a third bottom stream and a third top stream, wherein the third bottom stream comprises 1,3-dichloro-2-propanol and the third top stream comprises the olefin. At least a portion of the third top stream is returned to the first distillation column as the olefin stream.

In yet another aspect, an illustrative embodiment provides an apparatus for isolating 1,3-dichloro-2-propanol from a feed stream comprising of 2,2'-oxybis(1-chloropropane) and 1,3-dichloro-2-propanol. The apparatus comprises a first distillation column for separating the feed stream into at least a first top stream and a first bottom stream, using an olefin as an entrainer; and a second distillation column for separating the first top stream into a second top stream and a second bottom stream.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

In one aspect, a process is provided for using an olefin as an entrainer in an azeotropic distillation column in order to isolate a target organic compound.

Figure 1:
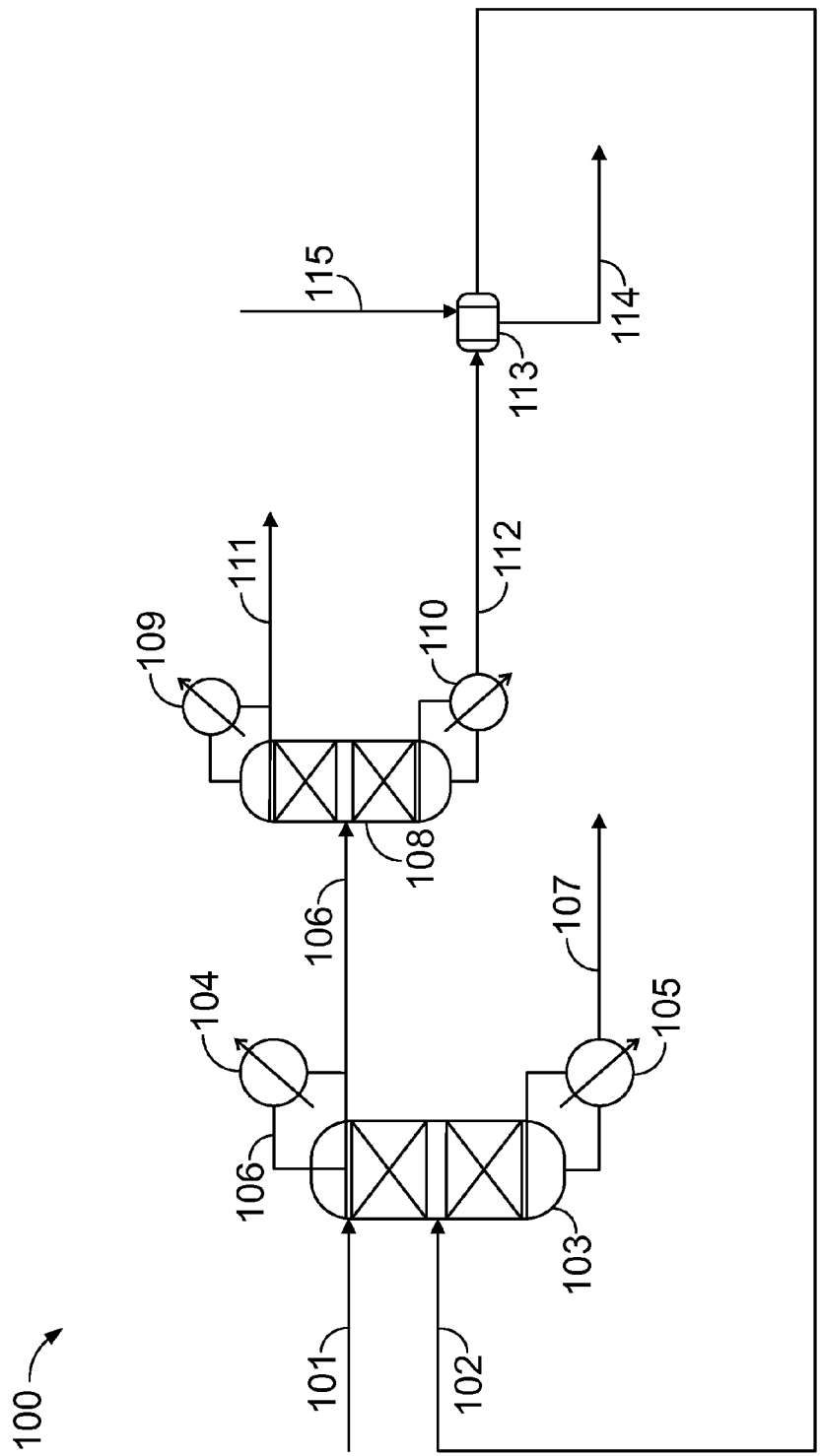
FIG. 1 is a schematic diagram of an apparatus for using an olefin as an entrainer to isolate a target organic compound, in accordance with an illustrative embodiment.

FIG. 1 illustrates an apparatus, 100, for isolating a target organic compound. The target organic compound may be a waste product of another process. For example, the target organic compound may be 1,3-dichloro-2-propanol (DCP). A possible source of DCP may be the distillation bottoms waste stream of a propylene oxide/propylene glycol process. This waste stream may contain residual epichlorohydrin, which can be converted to DCP by reacting with hydrogen chloride.

A feed stream 101 and a first olefin stream 102 may be supplied to a first distillation column 103. The feed stream 101 may comprise 2,2'-oxybis(1-chloropropane) and 1,3-dichloro-2-propanol. The first olefin stream 102 may comprise an olefin, such as 1-decene, 1-dodecene, or 1-tetradecene. The olefin may be a co-reactant in a further process, for example, a process for the etherification of DCP. (See, e.g., E. Daugs, D. Flick, C. Rand, M. Tulchinsky, W. Yu, United States Patent Application No. 2009/0281359 (2009)). Thus, an additional column for recovery of the olefin may not be required and any product contamination further downstream may be eliminated because of the use of a co-reactant. The ratio of the olefin stream 102 to the feed stream 101 may be about 0.01 or greater, more preferably about 0.05 or greater, and most preferably about 0.1 or greater. Further, the ratio of the olefin stream 102 to the feed stream 101 may be about 1 or less, more preferably about 0.5 or less, and most preferably about 0.3 or less.

The first distillation column 103 may be an azeotropic distillation column, such as a heterogeneous azeotropic distillation column. Heterogeneous azeotropic distillation columns may be used to separate mixtures of close relative volatility and also to break up azeotropes. The first distillation column 103 may comprise a first condenser 104 and a first reboiler 105.

In the first distillation column 103, the olefin may be used as an entrainer, such that the feed stream 101 is separated into at least a first top stream 106 and a first bottom stream 107. The olefin may form a minimum-boiling azeotrope with the target organic compound. The first top stream 106 may comprise the olefin and the target organic compound. The first bottom stream 107 may comprise a waste product, for example, 2,2'-oxybis(1-chloropropane).

The first top stream 106 may be condensed in the first condenser 104 and then may be supplied to a second distillation column 108. The second distillation column 108 may be a conventional distillation column. The second distillation column 108 may comprise a second condenser 109 and a second reboiler 110.

The second distillation column 108 may separate the first top stream 106 into at least a second top stream 111 and a second bottom stream 112. The second top stream 111 may comprise lighter boiling impurities such as 1,2-dichloropropane, residual epichlorohydrin, and 2-methyl-2-pentenal. The second bottom stream 112 may comprise a mixture of the olefin and the target organic compound.

The second bottom stream 112 may be supplied to a separator 113, where the second bottom stream 112 may be separated into a third bottom stream 114 and the first olefin stream 102. The separator 113 may be a decanter and may use liquid-liquid phase separation due to the density difference between DCP (1300 kg/m$^3$ (1.3 g/cc)) and olefin (700-800 kg/m$^3$ (0.7-0.8 g/cc)) and low mutual solubility. The third bottom stream 114 may comprise mostly the target organic compound. The first olefin stream 102 may return to the first distillation column 103. A second olefin stream 115 may be supplied to the separator 113 in order to replenish the olefin which may be lost in the first bottom stream 107 and the third bottom stream 114.

In an alternative embodiment, the olefin and the target organic compound may react in a reactor (not shown) instead of entering the separator 113.

EXAMPLES

Various examples of the invention are demonstrated. Examples 2, 4, 5, and 6 are generated using ASPEN computer-aided process simulation software (Aspen Technology, Incorporated, Burlington, Mass.), which uses a database of measured physical properties for engineering design calculations. Examples 1 and 3 are from laboratory experiments.

1,3-Dichloro-2-propanol (DCP) is a di-functional raw material available from epichlorohydrin-based chemistries that can be used for synthesis of a family of developmental new surfactant products based on etherification with olefins. (See, e.g., E. Daugs, D. Flick, C. Rand, M. Tulchinsky, W. Yu, United States Patent Application No. 2009/0281359 (2009)). DCP is available, for example, by purification from an intermediate stream in a process to prepare epichlorohydrin from glycerin (B. Hook, D. Tirtowidjojo, A. Merenov, WO2009126415 (2009)), or by titration of epichlorohydrin with hydrogen chloride.

Another possible source of DCP raw material is a waste stream from propylene oxide/propylene glycol (PO/PG) processes. This stream, often referred to as the Crude PDC (propylene dichloride) Bottoms, while containing only trace levels of DCP, contains residual epichlorohydrin that may be converted to DCP by reaction with hydrogen chloride. The accessible quantity of epichlorohydrin has been recovered from this stream by distillation. A summary of a typical stream composition of the Crude PDC Bottoms and the pure component boiling points at atmospheric pressure is shown in Table 1.

TABLE 1

Typical 1,2-Dichloropropane Bottoms Stream Composition

| Abbreviation | Compound | Boiling Point (degrees Celsius) | Area Percentage | Weight Percentage |
|---|---|---|---|---|
| PDC | 1,2-dichloropropane | 96 | 10.19 | 11.9 |
| 2M2P | 2-methyl-2-pentenal | 136 | 5.46 | 15.14 |
| Epi | Epichlorohydrin | 117 | 20.51 | 16.84 |
| PCH-1 | 1-chloro-2-propanol | 127 | 0.25 | 0.23 |
| PCH-2 | 2-chloro-1-propanol | 134 | 1.66 | 0.93 |
| TCP | 1,2,3-trichloropropane | 157 | 4.31 | 3.86 |
| DCIPE | 2,2'-oxybis(1-chloropropane) | 187 | 46.65 | 41.91 |
|  | Unknown | N/A | 0.49 | N/A |
|  | Unknown | N/A | 3.45 | N/A |
|  | Unknown | N/A | 5.12 | N/A |
| DCH-1 | 1,3-Dichloro-2-propanol | 174 | 0.45 | N/A |
| DCH-2 | 2,3-Dichloro-1-propanol | 184 | 0.18 | N/A |
|  | Unknown | N/A | 0.11 | N/A |
|  | Unknown | N/A | 0.74 | N/A |
|  | Unknown | N/A | 0.11 | N/A |

Example 1

Preparation and Distillation Purification of DCP from the Crude PDC Bottoms without an Azeotropic Entrainer A 1-L jacketed bottom-drain glass reactor with an overhead stirrer and nitrogen bubbler is charged with 0.8877 kg (887.7 grams) of the Crude PDC Bottoms, and cooled to 15 degrees Celsius using an attached recirculating heater/chiller. GC analysis of the feed solution finds 11.8 area percent dichloropropane, 22.8 area percent epichlorohydrin, 6.4 area percent 2-methyl-2-pentenal, 6.5 area percent (10.0 weight percent) 1,3-dichloro-2-propanol, 4.1 area percent 1,2,3-trichloropropane, and 46.0 area percent of 2,2'-oxybis(1-chloropropane). Hydrogen chloride gas (approximately 0.06 kg (60 grams)) from a lecture bottle on a balance is bubbled into the feed solution over about 3 hours. The clear solution turns yellow in color. The maximum temperature reached during the addition is 31 degrees Celsius. Gas chromatography (GC) analysis finds 11.8 area percent dichloropropane, 5.9 area percent epichlorohydrin, 6.4 area percent 2-methyl-2-pentenal, 19.7 area percent (27.6 weight percent) 1,3-dichloro-2-propanol, 3.0 area percent 1,2,3-trichloropropane, and 45.6 area percent of 2,2'-oxybis(1-chloropropane). After purging with nitrogen, the 0.9428 kg (942.8 gram) solution (mass increase of 0.0548 kg (54.8 grams)) is removed and is charged to a magnetically stirred 2-L round-bottom flask in a heating mantle equipped with a 14 inch vacuum jacketed ceramic saddle-packed distillation column and a reflux control head. The solution is distilled at atmospheric pressure with a 5:1 reflux ratio to collect four distillate fractions. Distillation conditions and analysis results are summarized in Table 2.

TABLE 2

Distillation of the HCl Treated Crude PDC Bottoms

|  | Feed | Fraction 1 | Fraction 2 | Fraction 3 | Fraction 4 | Bottoms |
|---|---|---|---|---|---|---|
| Distillation Conditions |  |  |  |  |  |  |
| Bottoms Temperature (degrees Celsius) |  | 152-180 | 180-182 | 182-185 | 186-190 |  |
| Overheads Temperature |  | 84-164 | 164-171 | 170-175 | 177-180 |  |
| Percent of Mass Charge |  | 26% | 14% | 17% | 16% | 27% |
| GC Area Percent of (Compound) |  |  |  |  |  |  |
| 1,2-dichloropropane | 11.8 | 48 | 0.3 | 0.2 | <0.1 | <0.1 |
| 2-methyle-2-pentenal | 6.4 | 12.7 | 22.9 | 9.9 | 5.1 | 1.5 |
| Epichlorohydrin | 5.9 | 22 | 1.6 | 0.1 | 0.2 | <0.1 |
| 1,2,3-trichloropropane | 3 | 5.7 | 2.8 | 1.6 | 1.0 | 0.6 |
| 2,2'-oxybis(1-chloropropane) | 45.6 | 6.1 | 33.3 | 49.7 | 65.6 | 76.4 |
| Weight Percent 1,3-dichloro-2-propanol | 27.6% | 7.7% | 47.5% | 44.9% | 35.1% | 4.1% |

After removal of the bulk of the lighter components in Fraction 1, three fractions are collected at the approximate boiling point of DCP. However, all three fractions show significant contamination by 2,2'-oxybis(1-chloropropane) ("bis-ether"), which is the major component of the waste stream.

Figure 2:
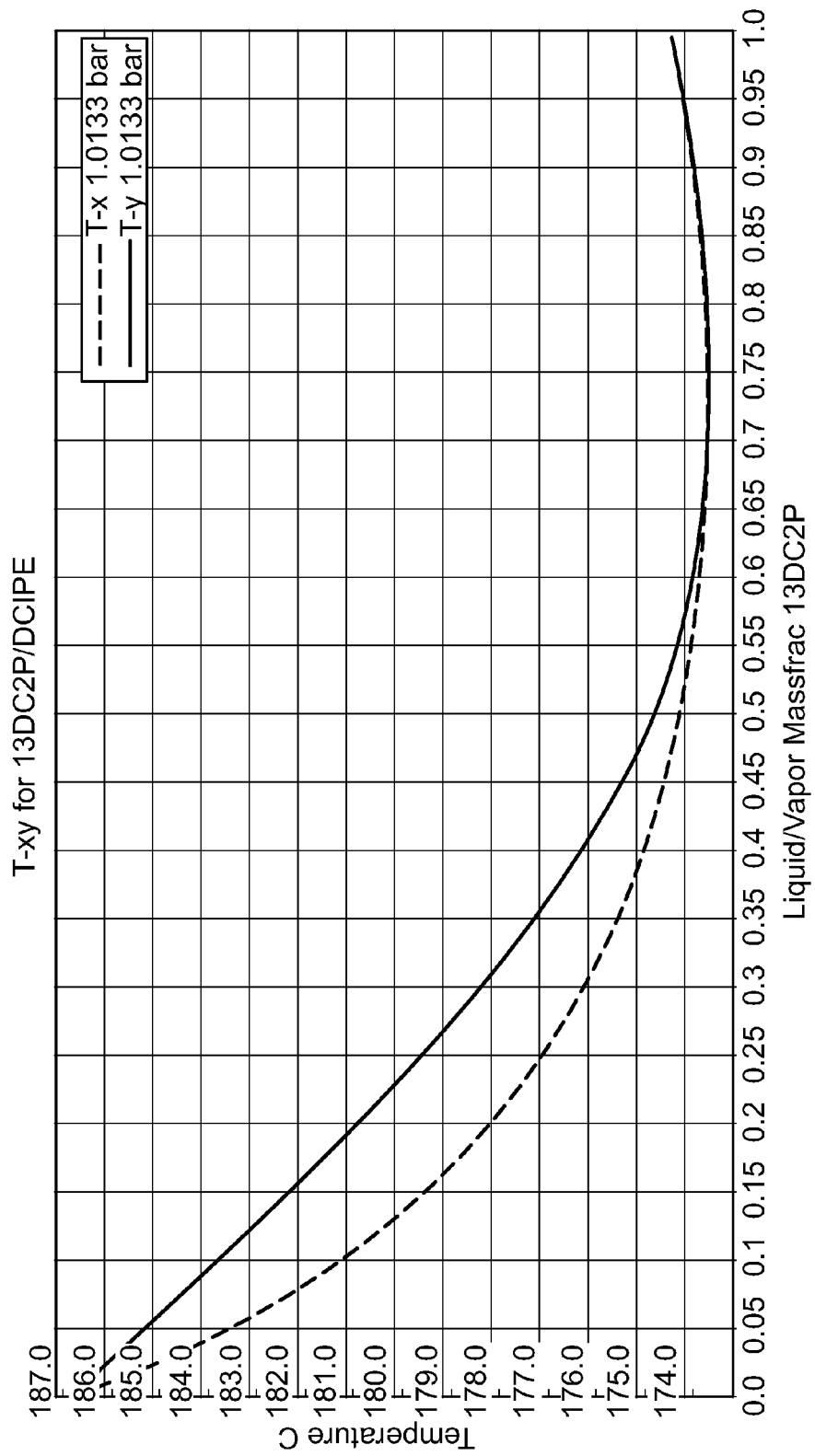
FIG. 2 is a graph of a vapor-liquid equilibrium model assessment of 1,3-dichloro-2-propanol and 2,2'-oxybis(1-chloropropane).

Assessment of the 2-component system of DCP and the bis-ether by the UNIFAC group contribution method vapor liquid equilibrium (VLE) model predicts a minimum-boiling azeotrope for the DCP and bis-ether at 174 degrees Celsius at atmospheric pressure (FIG. 2). Presence of this azeotrope complicates separation of the two species by distillation.

Figure 3:
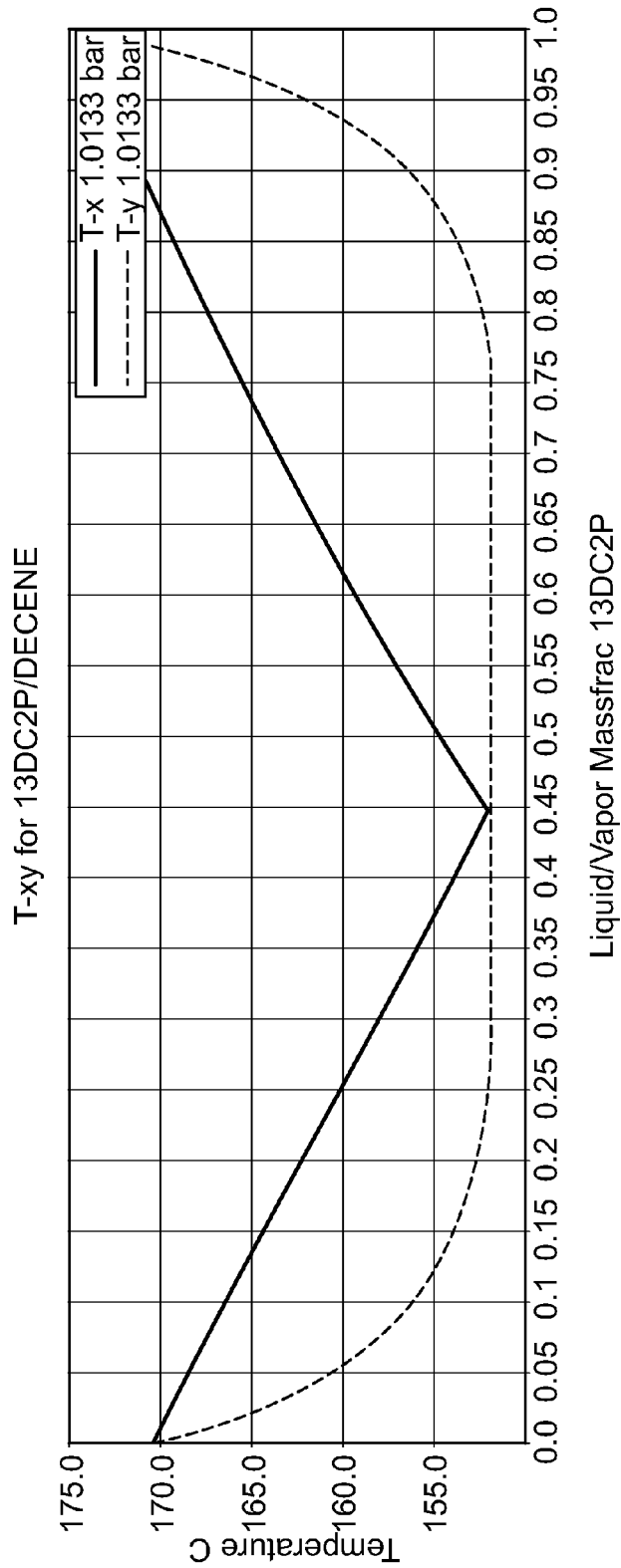
FIG. 3 is a graph of a vapor-liquid equilibrium model assessment of 1,3-dichloro-2-propanol and 1-decene.

A minimum-boiling azeotrope is also predicted for the two component system of 1,3-dichloro-2-propanol and 1-decene (FIG. 3). Since the ether [2-chloro-1-(chloromethyl)ethoxy]-decane is of value for preparation of new surfactant products and is produced using 1-decene as raw material, using 1-decene also as a separating agent may be practical method to isolate DCP from the HCl-treated Crude PDC Bottoms stream (see Examples 2 and 3).

Example 2

Case I: Conceptual Scheme for Azeotropic Distillation of DCP Using 1-Decene—Process Simulation A conceptual process flow scheme for purification of DCP from the HCl-treated PO/PG waste stream using 1-decene as an azeotropic entrainer is developed using ASPEN process simulation software version 2006.5. The Universal Functional Activity Coefficient (UNIFAC) predicted azeotropic composition of decene-DCP (47 mole percent DCP) is an equimolar ratio of decene to DCP in the final purified stream (FIG. 3), which would be a good feed composition for the reactive etherification process to produce the ether [2-chloro-1-(chloromethyl)ethoxy]-decane. Table 3 shows the composition of the feed stream following HCl treatment.

TABLE 3

Design basis HCl-treated Crude PDC Bottoms stream composition

| Component | Weight Percent | kg/h |
|---|---|---|
| 1,2-dichloropropane | 5 | 100 |
| Epichlorohydrin | 3 | 60 |
| 2-methyl-2-pentenal | 7 | 140 |
| 1,3-dichloro-2-propanol | 27 | 540 |
| 2,2'-oxybis(1-chloropropane) | 54 | 1080 |
| 1,2,3-trichloropropane | 4 | 80 |

Column 1 is an azeotropic distillation column with 30 equilibrium contacting trays or stages, where 1-decene entrains the DCP in the HCl-treated PO/PG waste stream and carries it overhead and the heavier boiling 2,2'-oxybis(1-chloropropane) (bis-ether) is separated as a bottoms fraction. Predicted stream details for Column 1 are shown in Table 4.

TABLE 4

Column 1 process simulation details (1-decene as entrainer)

| | FEED | ENTRAINER | BOTTOMS1 | OVERHEAD1 |
|---|---|---|---|---|
| Temperature (degrees Celsius) | 50 | 50 | 186 | 139.4 |

TABLE 4-continued

Column 1 process simulation details (1-decene as entrainer)

| | FEED | ENTRAINER | BOTTOMS1 | OVERHEAD1 |
|---|---|---|---|---|
| Pressure (Pascal) | 1.01E5 | 1.01E5 | 1.01E5 | 1.01E5 |
| Vapor Fraction | 0 | 0 | 0 | 0 |
| Mole Flow (mol/h) | 14000.0 | 4200.0 | 6400.0 | 11800.0 |
| Mass Flow (kg/h) | 2000.0 | 590.0 | 1089.6 | 1500.4 |
| Volume Flow (cubic meters/h) | 1.8 | 0.8 | 1.2 | 1.8 |
| Mass Flow (kg/h) | | | | |
| 1,2-dichloropropane | 100 | 0 | 0 | 100 |
| Epichlorohydrin | 60 | 0 | 0 | 60 |
| 2-methyl-2-pentenal | 140 | 0 | 0 | 140 |
| 1,3-dichloro-2-propanol | 540 | 0 | 5.4 | 534.6 |
| 2,2'-oxybis(1-chloropropane) | 1080 | 0 | 1077.8 | 2.2 |
| 1,2,3-trichloropropane | 80 | 0 | 1.7 | 78.3 |
| 1-decene | 0 | 590 | 4.6 | 585.4 |
| Mass Fraction | | | | |
| 1,2-dichloropropane | 0.05 | 0 | 0 | 0.067 |
| Epichlorohydrin | 0.03 | 0 | 0 | 0.04 |
| 2-methyl-2-pentenal | 0.07 | 0 | 0 | 0.093 |
| 1,3-dichloro-2-propanol | 0.27 | 0 | 0.005 | 0.356 |
| 2,2'-oxybis(1-chloropropane) | 0.54 | 0 | 0.989 | 0.001 |
| 1,2,3-trichloropropane | 0.04 | 0 | 0.002 | 0.052 |
| 1-decene | 0 | 1 | 0.004 | 0.39 |

Column 1 is operated at a design specification of 99 percent mass recovery of DCP in the overheads and 99.8 percent removal of the bis-ether from bottoms, which requires a reflux ratio (mass) of approximately 3 or a duty of $1.219 \times 10^6$ J/kg (1155 Btu/kg) HCl treated stream. The laboratory trial in Example 3 corresponds to the distillation in Column 1, where almost all of the 2-methyl-2-pentenal is obtained in the overheads, along with 1-decene and DCP.

Column 2 separates the lighter boiling 1,2-dichloropropane, residual epichlorohydrin, and 2-methyl-2-pentenal in the overheads and obtains 1-decene and DCP at the bottom. Stream details for Column 2 are shown in Table 5.

TABLE 5

Column 2 process simulation details (1-decene as entrainer)

| | OVERHEAD1 | OVERHEAD2 | BOTTOMS2 |
|---|---|---|---|
| Temperature (degrees Celsius) | 139.4 | 115.8 | 151.7 |
| Pressure (Pascal) | 1.0E5 | 1.0E5 | 1.0E5 |
| Vapor Fraction | 0.0 | 0.0 | 0.0 |
| Mole Flow (mol/h) | 11800.0 | 3400.0 | 8400.0 |
| Mass Flow (kg/h) | 1500.8 | 360.5 | 1140.4 |
| Volume Flow (cubic meters/h) | 1.8 | 0.4 | 1.4 |
| Mass Flow (kg/h) | | | |
| 1,2-dichloropropane | 100.0 | 100.0 | 0.0 |
| Epichlorohydrin | 60.0 | 60.0 | 0.0 |
| 2-methyl-2-pentenal | 140.0 | 139.3 | 0.7 |

TABLE 5-continued

Column 2 process simulation details (1-decene as entrainer)

| | OVERHEAD1 | OVERHEAD2 | BOTTOMS2 |
|---|---|---|---|
| 1,3-dichloro-2-propanol | 534.6 | 32.8 | 501.8 |
| 2,2'-oxybis(1-chloropropane) | 2.16 | 0.0 | 2.16 |
| 1,2,3-trichloropropane | 78.7 | 22.55 | 56.2 |
| 1-decene | 585.4 | 5.9 | 579.5 |
| Mass Fraction | | | |
| 1,2-dichloropropane | 0.067 | 0.277 | 0 |
| Epichlorohydrin | 0.04 | 0.166 | 0 |
| 2-methyl-2-pentenal | 0.093 | 0.386 | 0.001 |
| 1,3-dichloro-2-propanol | 0.356 | 0.091 | 0.44 |
| 2,2'-oxybis(1-chloropropane) | 0.001 | 0 | 0.002 |
| 1,2,3-trichloropropane | 0.052 | 0.063 | 0.049 |
| 1-decene | 0.39 | 0.016 | 0.508 |

Figure 4:
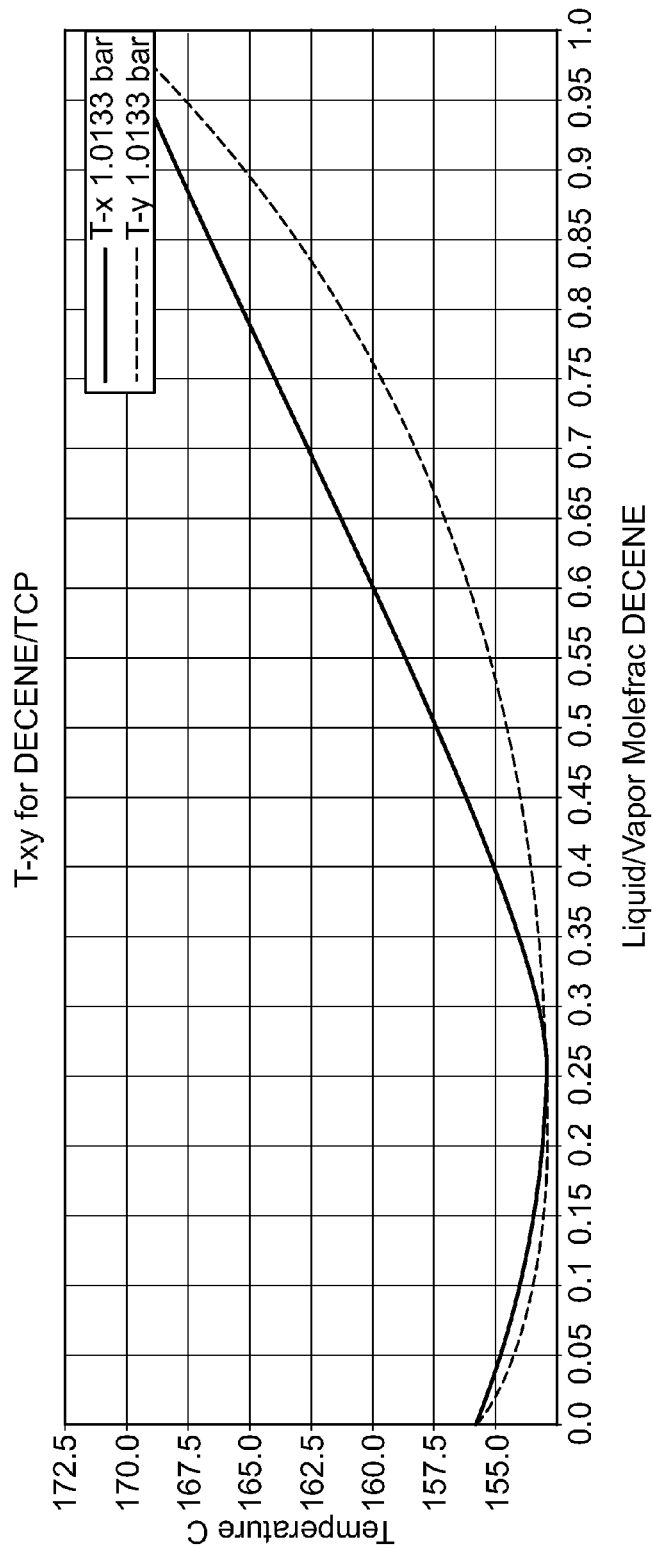
FIG. 4 is a graph of a vapor-liquid equilibrium model assessment of 1,2,3-trichloropropane and 1-decene.

Column 2, consisting of 30 equilibrium contacting stages or trays, is operated at a design specification of 99 percent recovery of the incoming 1-decene in the bottoms and 99.5 percent recovery of 2-methyl-2-pentenal in the overheads. This requires a reflux ratio (mass) of 7.3 or a duty of $5.28 \times 10^5$ J/kg (500 Btu/kg) HCl treated stream. The stream Bottoms2 containing 1-decene and DCP is then cooled and sent to decanter wherein it separates into two liquid phases—the lighter phase containing 1-decene is recycled back and the heavier phase containing DCP is the desired purified product (see Table 6). As a process alternative, the Bottoms2 stream may be the feed for the reactive etherification to produce the ether [2-chloro-1-(chloromethyl)ethoxy]-decane. A makeup stream (about 28.2+4.6+5.8 kg/h) refurbishes the total 1-decene, which is entrained along with final DCP stream, the bis-ether bottoms from Column 1, and the overheads from Column 2 An overall recovery of 93.5 percent DCP is obtained. Stream details for Column 2 are shown in Table 5. It is worth noting here that only about 50 percent of the incoming TCP (impurity) is removed in the overheads, since 1-decene forms a minimum-boiling azeotrope with TCP as shown in FIG. 4.

The most significant impurity is predicted to be 1,2,3-trichloropropane, at approximately 4 weight percent. An overall recovery of 93.5 percent DCP and 98.2 percent 1-decene is predicted from the process simulation. An olefin (entrainer) to DCP in feed mass ratio of 0.3-1.5 is preferred for 1-decene as an entrainer.

TABLE 6

Decanter stream details (1-decene as entrainer)

| | BOTTOMS2 | DCP | OLEFIN |
|---|---|---|---|
| Temperature (degrees Celsius) | 151.8 | −10.0 | −10.0 |
| Pressure (Pascal) | 1.0E5 | 1.0E5 | 1.0E5 |
| Vapor Fraction | 0.0 | 0.0 | 0.0 |
| Mole Flow (mol/h) | 8300.0 | 4100.0 | 4300.0 |
| Mass Flow (kg/h) | 1140.4 | 533.5 | 606.9 |
| Volume Flow (cubic meters/h) | 1.4 | 0.4 | 0.8 |

TABLE 6-continued

Decanter stream details (1-decene as entrainer)

| | BOTTOMS2 | DCP | OLEFIN |
|---|---|---|---|
| Mass Flow (kg/h) | | | |
| 1,2-dichloropropane | 0.0 | 0.0 | 0.0 |
| Epichlorohydrin | 0.0 | 0.0 | 0.0 |
| 2-methyl-2-pentenal | 0.7 | 0.1 | 0.6 |
| 1,3-dichloro-2-propanol | 501.8 | 475.4 | 26.4 |
| 2,2'-oxybis(1-chloropropane) | 2.2 | 1.5 | 0.6 |
| 1,2,3-trichloropropane | 56.2 | 28.2 | 28.0 |
| 1-decene | 579.5 | 28.2 | 551.4 |
| Mass Fraction | | | |
| 1,2-dichloropropane | 0 | 0 | 0 |
| Epichlorohydrin | 0 | 0 | 0 |
| 2-methyl-2-pentenal | 0.001 | 0 | 0.001 |
| 1,3-dichloro-2-propanol | 0.447 | 0.904 | 0.043 |
| 2,2'-oxybis(1-chloropropane) | 0.002 | 0.003 | 0.001 |
| 1,2,3-trichloropropane | 0.038 | 0.04 | 0.035 |
| 1-decene | 0.513 | 0.052 | 0.92 |

Example 3

Preparation and Distillation Purification of DCP from the Crude PDC Bottoms Stream with 1-Decene as an Azeotropic Entrainer A 1-L jacketed bottom-drain glass reactor with an overhead stirrer and nitrogen bubbler is charged with 0.8453 kg (845.3 grams) of the Crude PDC Bottoms stream, and is cooled to 8 degrees Celsius using an attached recirculating heater/chiller. Hydrogen chloride gas (approximately 0.070 kg (70 grams)) from a lecture bottle on a balance is slowly bubbled in. The clear solution turns yellow in color. The maximum temperature reached during the addition is 40 degrees Celsius. GC analysis finds 12.0 area percent dichloropropane, 2.9 area percent epichlorohydrin, 6.6 area percent 2-methyl-2-pentenal, 17.6 area percent (24.4 weight percent) 1,3-dichloro-2-propanol, 4.6 area percent 1,2,3-trichloropropane, and 46.1 area percent of 2,2'-oxybis(1-chloropropane). After purging with nitrogen, the 0.8989 kg (898.9 gram) solution (mass increase of 0.0536 kg (53.6 grams)) is removed and charged with 0.276 kg (276 grams) of 1-decene to a magnetically stirred 2-L round-bottom flask in a heating mantle equipped with a 0.36 meter (14 inch) vacuum jacketed ceramic saddle-packed distillation column and a reflux control head. The solution is distilled at atmospheric pressure with a 5:1 reflux ratio to collect seven distillate fractions. Distillation conditions and analysis results are summarized in Table 7.

TABLE 7

Distillation of the HCl treated stream with 1-decene

|  | Fraction 1 | Fraction 2 | Fraction 3 | Fraction 4 | Fraction 5 | Fraction 6 | Fraction 7 | Bottoms |
|---|---|---|---|---|---|---|---|---|
| Distillation Conditions | | | | | | | | |
| Bottoms Temperature (degrees Celsius) | 154-163 | 166-169 | 169 | 170 | 171 | 171 | 170 | |
| Overheads Temperature (degrees Celsius) | 59-85 | 119-153 | 154-155 | 156 | 156 | 156-157 | 156 | |
| Percent of Mass Change | 6% | 7% | 4% | 5% | 4% | 1% | 18% | 50% |
| GC Area Percent of (Compound) | | | | | | | | |
| 1,2-dichloropropane | 82.6 | 22.8 | 0.4 | <0.1 | <0.1 | Not Analyzed | <0.1 | <0.1 |
| 2-methyl-2-pentenal | 0.9 | 7.5 | 11.2 | 11.4 | 9.3 | Not Analyzed | 6.5 | 1 |
| Epichlorohydrin | 8.6 | 12.4 | 2 | 0.7 | 0.6 | Not Analyzed | 0.2 | <0.1 |
| 1,2,3-trichloropropane | 0.8 | 2.9 | 4.6 | 0.2 | 4.4 | Not Analyzed | 3.4 | <0.1 |
| 2,2'-oxybis(1-chloropropane) | <0.1 | 1.3 | 2.4 | 2.6 | 2.5 | Not Analyzed | 3.1 | 51.8 |
| 1,3-dichloro-2-propanol | 0.3 | 4.9 | 9.2 | 4.9 | 10.1 | Not Analyzed | 11.4 | 11.5 |
| 1-decene | 5.4 | 45.5 | 69.8 | 79.8 | 72.5 | Not Analyzed | 74.6 | 29.9 |
| Weight percent 1,3-dichloro-2-propanol | 1.1% | 10.3% | 24.1% | 12.0% | 26.2% | | 30.0% | 21.4% |
| Weight percent 1-decene | 1.8% | 18.0% | 35.6% | 38.0% | 36.7% | | 38.6% | 10.5% |

Figure 5:
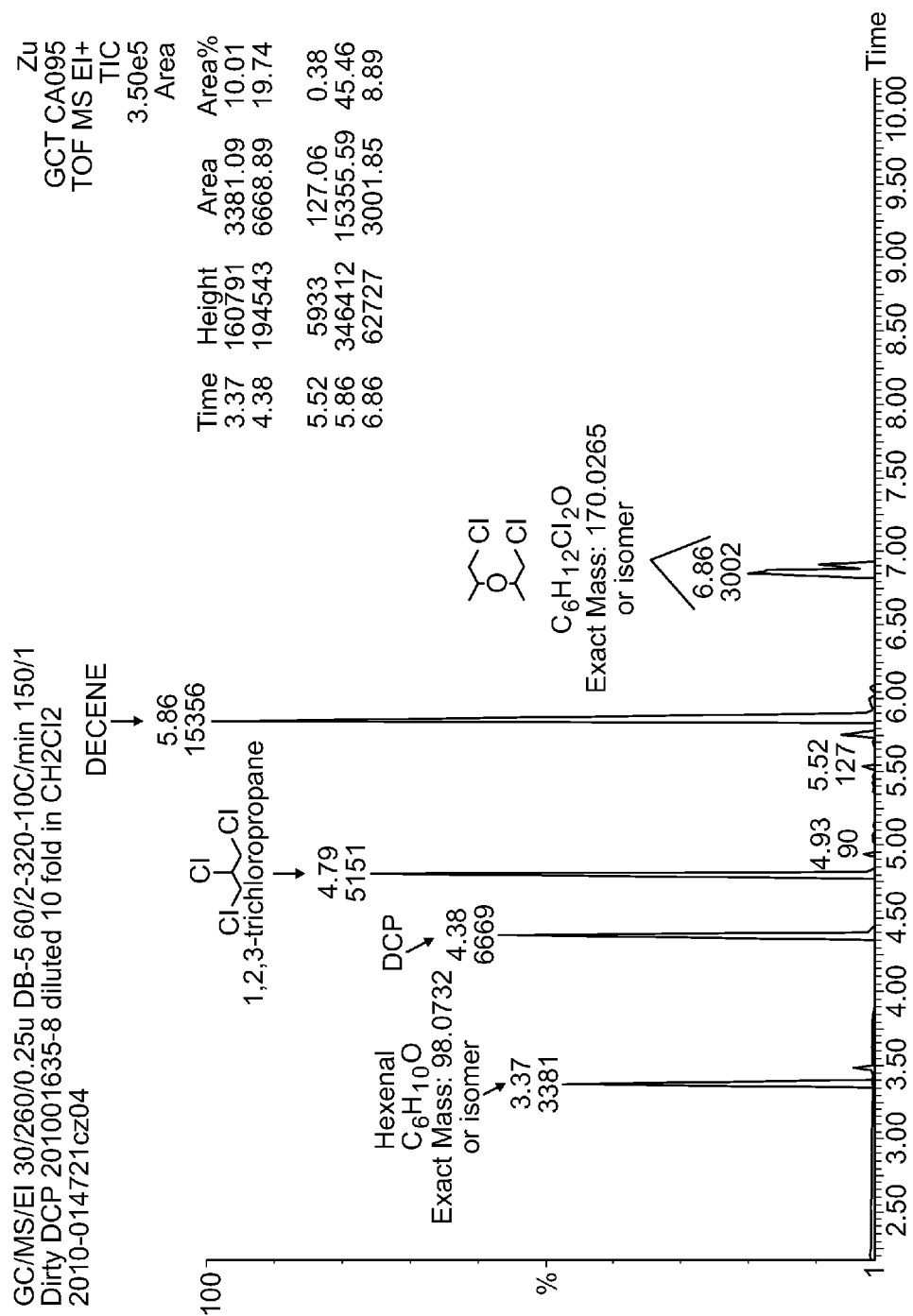
FIG. 5 is a graph of a gas chromatography/mass spectrometry (GC/MS) analysis of a 1,3-dichloro-2-propanol/1-decene distillate fraction.

An azeotrope of DCP and 1-decene are distilled from the mixture. The product-containing distillate fractions are collected at a lower temperature, and contain approximately equal parts of DCP and 1-decene. The main product fraction (Fraction 7 of Table 7) is analyzed by GC/MS analysis for confirmation of component identification (FIG. 5).

Example 4

Case II: 1-Dodecene as Entrainer

Figure 6:
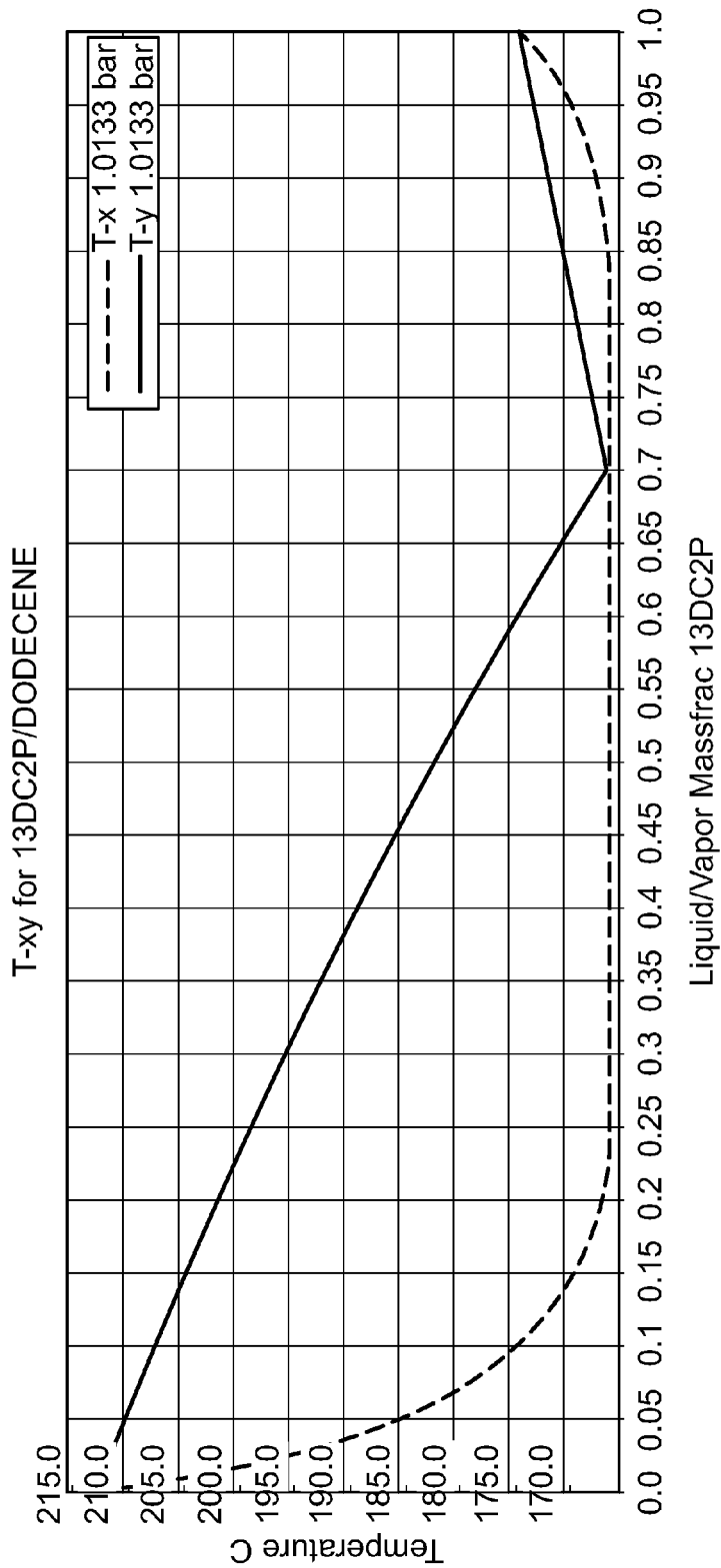
FIG. 6 is a graph of a vapor-liquid equilibrium model assessment of 1,3-dichloro-2-propanol and 1-dodecene.

In addition to 1-decene, 1-dodecene may also be used as an entrainer for DCP (see FIG. 6). Column 1 is the azeotropic distillation column comprising 30 equilibrium contacting stages or trays, wherein 1-dodecene entrains the DCP in the HCl-treated feed stream (from Table 3) and carries it overhead, whereas the heavier boiling bis-ether is obtained as bottoms. Column 1 is operated at a design specification of 99 percent mass recovery of DCP in the overheads and 99.9 percent removal of the bis-ether from bottoms—which requires a reflux ratio (mass) of about 6 or a duty of $1.556 \times 10^6$ J/kg (1475 Btu/kg) HCl treated stream. Stream details for Column 1 are shown in Table 8.

TABLE 8

Column 1 process simulation details (1-dodecene as entrainer)

|  | FEED | ENTRAINER | BOTTOMS1 | OVERHEAD1 |
|---|---|---|---|---|
| Temperature (degrees Celsius) | 50 | 50 | 186.5 | 137.4 |
| Pressure (Pascal) | $1.01 \times 10^5$ | $1.01 \times 10^5$ | $1.01 \times 10^5$ | $1.01 \times 10^5$ |
| Vapor Fraction | 0 | 0 | 0 | 0 |
| Mole Flow (mol/h) | 14002.0 | 1200.0 | 6376.0 | 8826.0 |
| Mass Flow (kg/h) | 2000.0 | 202 | 1088.765 | 1113.235 |
| Volume Flow (cubic meters/h) | 1.772 | 0.274 | 1.171 | 1.171 |
| Mass Flow (kg/h) | | | | |
| 1,2-dichloropropane | 100.0 | 0.0 | 0.0 | 100.0 |
| Epichlorohydrin | 60.0 | 0.0 | 0.0 | 60.0 |
| 2-methyl-2-pentenal | 140.0 | 0.0 | 0.0 | 140.0 |
| 1,3-dichloro-2-propanol | 540.0 | 0.0 | 5.4 | 534.6 |
| 2,2'-oxybis(1-chloropropane) | 1080.0 | 0.0 | 1078.9 | 1.1 |

TABLE 8-continued

Column 1 process simulation details (1-dodecene as entrainer)

|  | FEED | EN-TRAIN-ER | BOT-TOMS1 | OVER-HEAD1 |
|---|---|---|---|---|
| 1,2,3-trichloropropane | 80.0 | 0.0 | 0.9 | 79.1 |
| 1-dodecene | 0.0 | 202.0 | 3.5 | 198.5 |
| Mass Fraction |  |  |  |  |
| 1,2-dichloropropane | 0.05 | 0 | 0 | 0.09 |
| Epichlorohydrin | 0.03 | 0 | 0 | 0.054 |
| 2-methyl-2-pentenal | 0.07 | 0 | 0 | 0.126 |
| 1-dodecene | 0 | 1 | 0.003 | 0.178 |
| 1,3-dichloro-2-propanol | 0.27 | 0 | 0.005 | 0.48 |
| 2,2'-oxybis(1-chloropropane) | 0.54 | 0 | 0.991 | 0.001 |
| 1,2,3-trichloropropane | 0.04 | 0 | 0.001 | 0.071 |

Further downstream, Column 2 separates the lighter boiling impurities—1,2-dichloropropane, epichlorohydrin, 2-methyl-2-pentenal, 1,2,3-trichloropropane—in the overheads and obtains 1-dodecene and DCP at the bottom. Column 2, consisting of 30 equilibrium contacting stages or trays is operated at a design specification of 99.5 percent recovery of the incoming 1-dodecene in the bottoms and 99.5 percent recovery of 1,2,3-trichloropropane in overheads. This requires a reflux ratio (mass) of about 12.1 or a duty of about $9.34 \times 10^5$ J/kg (885 Btu/kg) HCl treated stream. Stream details for Column 2 are shown in Table 9.

TABLE 9

Column 2 process simulation details (1-dodecene as entrainer)

|  | OVERHEAD1 | OVERHEAD2 | BOTTOMS2 |
|---|---|---|---|
| Temperature (degrees Celsius) | 137.4 | 118.2 | 166.3 |
| Pressure (Pascal) | $1.01 \times 10^5$ | $1.01 \times 10^5$ | $1.01 \times 10^5$ |
| Vapor Fraction | 0.0 | 0.0 | 0.0 |
| Mole Flow (mol/h) | 8800.0 | 3800.0 | 5000.0 |
| Mass Flow (kg/h) | 1113.2 | 416.4 | 696.9 |
| Volume Flow (cubic meters/h) | 1.2 | 0.4 | 0.7 |
| Mass Flow (kg/h) |  |  |  |
| 1,2-dichloropropane | 100.0 | 100.0 | 0.0 |
| Epichlorohydrin | 60.0 | 60.0 | 0.0 |
| 2-methyl-2-pentenal | 140.0 | 140.0 | 0.0 |
| 1,3-dichloro-2-propanol | 534.6 | 36.7 | 497.9 |
| 2,2'-oxybis(1-chloropropane) | 1.1 | 0.0 | 1.1 |
| 1,2,3-trichloropropane | 79.1 | 78.7 | 0.4 |
| 1-dodecene | 198.5 | 1.0 | 197.5 |
| Mass Fraction |  |  |  |
| 1,2-dichloropropane | 0.09 | 0.24 | 0 |
| Epichlorohydrin | 0.054 | 0.144 | 0 |
| 2-methyl-2-pentenal | 0.126 | 0.336 | 0 |
| 1,3-dichloro-2-propanol | 0.48 | 0.088 | 0.714 |
| 2,2'-oxybis(1-chloropropane) | 0.001 | 0 | 0.002 |
| 1,2,3-trichloropropane | 0.071 | 0.189 | 0.001 |
| 1-dodecene | 0.178 | 0.002 | 0.283 |

The stream Bottoms2 containing 1-dodecene and DCP is then cooled and sent to decanter wherein it separates into two liquid phases—the lighter phase containing 1-dodecene is recycled back and the heavier phase containing DCP is the purified product (see Table 10). As a process alternative, the Bottoms2 stream may be the feed for the reactive etherification to produce the ether [2-chloro-1-(chloromethyl)ethoxy]-dodecane. A makeup stream (14.1+3.5+1 kg/h) refurbishes the 1-dodecene which is entrained along with final DCP stream, the bis-ether bottoms from Column 1, and overheads from Column 2. An overall recovery of 92 percent DCP is obtained.

TABLE 10

Decanter stream details (1-dodecene as entrainer)

|  | BOTTOMS2 | LIQUID1 | LIQUID2 |
|---|---|---|---|
| Temperature (degrees Celsius) | 166.3 | −10 | −10 |
| Pressure (Pascal) | $1.01 \times 10^5$ | $1.01 \times 10^5$ | $1.01 \times 10^5$ |
| Vapor Fraction | 0 | 0 | 0 |
| Mole Flow (mol/h) | 5042.0 | 3908.0 | 1135.0 |
| Mass Flow (kg/h) | 696.87 | 507.619 | 189.251 |
| Volume Flow (cubic meters/h) | 0.74 | 0.373 | 0.239 |
| Mass Flow (kg/h) |  |  |  |
| 1,2-dichloropropane | 0 | 0 | 0 |
| Epichlorohydrin | 0.001 | 0.001 | 0 |
| 2-methyl-2-pentenal | 0.002 | 0.001 | 0 |
| 1,3-dichloro-2-propanol | 497.86 | 492.209 | 5.652 |
| 2,2'-oxybis(1-chloropropane) | 1.08 | 0.992 | 0.089 |
| 1,2,3-trichloropropane | 0.395 | 0.309 | 0.087 |
| 1-dodecene | 197.531 | 14.109 | 183.423 |
| Mass Fraction |  |  |  |
| 1,2-dichloropropane | 0 | 0 | 0 |
| Epichlorohydrin | 0 | 0 | 0 |
| 2-methyl-2-pentenal | 0 | 0 | 0 |
| 1,3-dichloro-2-propanol | 0.714 | 0.97 | 0.03 |
| 2,2'-oxybis(1-chloropropane) | 0.002 | 0.002 | 0 |
| 1,2,3-trichloropropane | 0.001 | 0.001 | 0 |
| 1-dodecene | 0.283 | 0.028 | 0.969 |

Figure 7:
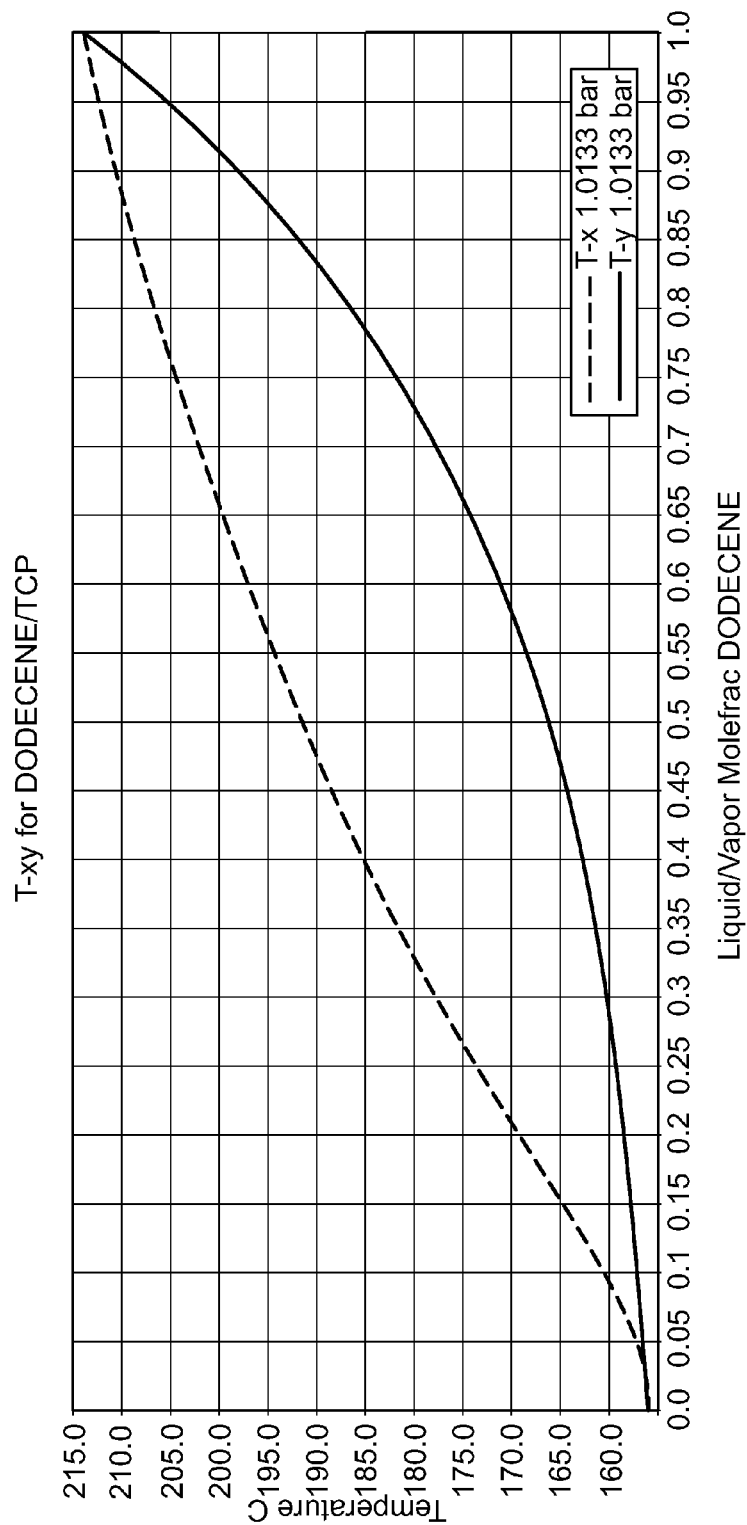
FIG. 7 is a graph of a vapor-liquid equilibrium model assessment of 1,2,3-trichloropropane and 1-dodecene.

1-Dodecene has an advantage over 1-decene because when 1-dodecene is used as an entrainer, almost all of the 1,2,3-trichloropropane and 2-methyl-2-pentenal impurities are removed in the overhead stream. This is because TCP does not form an azeotrope with 1-dodecene (see FIG. 7), as it does with 1-decene. In addition, a lower entrainer to feed ratio (mass)—about 0.4—is required with 1-dodecene, as compared to an entrainer to feed ratio (mass) of about 1 with 1-decene. The entrainer loss is also lower, and therefore a smaller makeup stream is required with 1-dodecene.

Example 5

Case III: 1-Tetradecene as Entrainer

Figure 8:
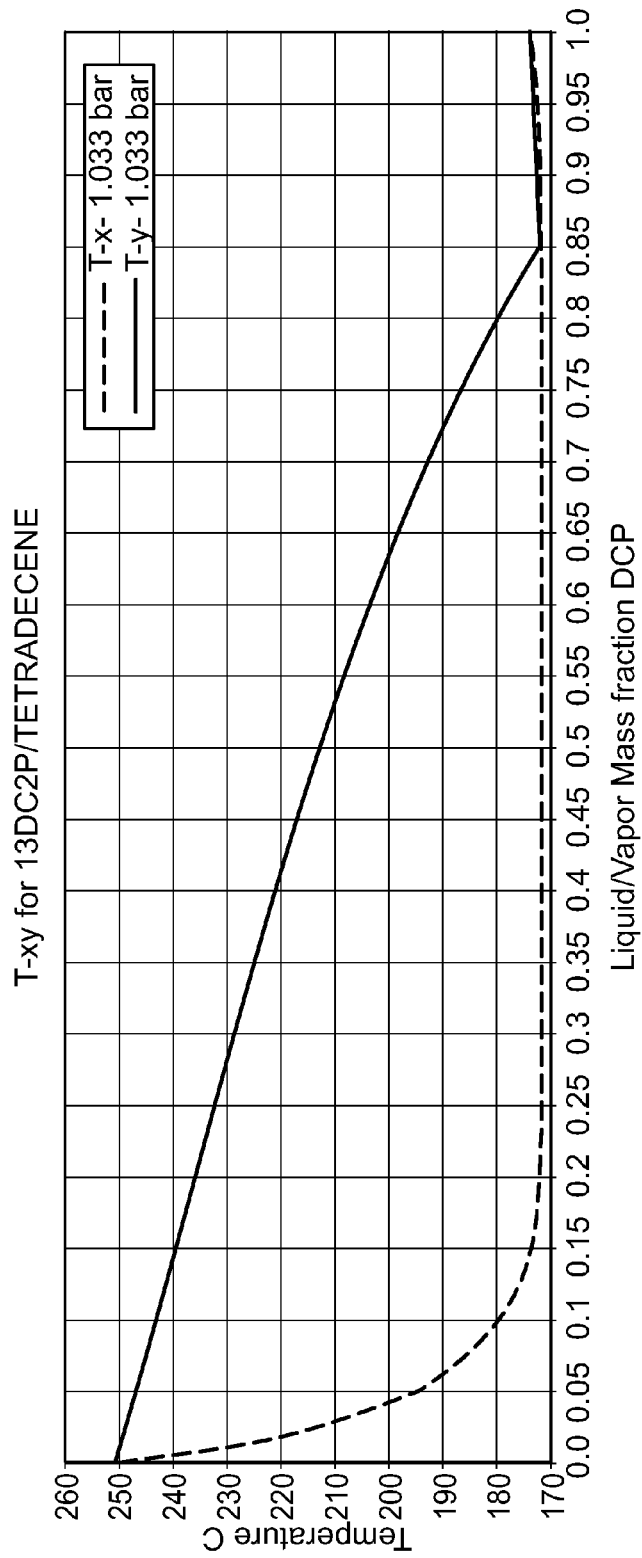
FIG. 8 is a graph of a vapor-liquid equilibrium model assessment of 1,3-dichloro-2-propanol and 1-tetradecene.

In addition to 1-decene and 1-dodecene, 1-tetradecene may also be used as an entrainer for DCP (see FIG. 8), although it does not remove as much of the bis-ether. Column 1 is the azeotropic distillation column, wherein 1-tetradecene entrains the DCP in the HCl-treated feed stream (from Table 3) and carries it overhead, whereas the heavier boiling bis-ether is obtained as bottoms. Column 1—consisting of 30 equilibrium contacting stages or trays, is operated at a design specification of 99 percent mass recovery of DCP in the overheads, which requires a reflux ratio (mass) of about 10 or a duty of $2.235 \times 10^6$ J/kg (2118 Btu/kg) HCl treated stream (see Table 11). The use of 1-tetradecene allows for about 93 percent removal of incoming bis-ether, beyond which the 1-tetradecene entrainer begins to appear in the bottoms and would then require an additional column to recover and recycle back to the azeotropic distillation column. Further downstream, Column 2 separates the lighter boiling impurities 1,2-dichloropropane, epichlorohydrin, 2-methyl-2-pentenal, 1,2,3-trichloropropane in the overheads, and generates 1-tetradecene, DCP, and entrained bis-ether at the bottom. Column 2, consisting of 30 equilibrium contacting stages or trays, is operated at a design specification of 97.5 percent recovery of the incoming DCP in the bottoms and 99.5 percent recovery of 1,2,3-trichloropropane in overheads. This requires a reflux ratio (mass) of about 2.4, or a duty of about $2.43 \times 10^5$ J/kg (230 Btu/kg) HCl treated stream (see Table 12). The stream Bottoms2 containing 1-tetradecene and DCP is then cooled and sent to decanter wherein it separates into two liquid phases, the lighter phase containing 1-tetradecene is recycled back and the heavier phase containing the purified DCP product (see Table 13). As a process alternative, the Bottoms2 stream may be the feed for the reactive etherification to produce the ether [2-chloro-1-(chloromethyl)ethoxy]-tetradecane. The unrecovered bis-ether eventually appears in the final DCP stream (after phase separation), which is undesirable. A makeup stream (5.4+12.6 kg/h) refurbishes the 1-tetradecene which is entrained along with final DCP stream, the bis-ether bottoms from Column 1, and the overheads from Column 2. An overall recovery of 96 percent DCP is obtained.

TABLE 11

Column 1 process simulation details (1-tetradecene as entrainer).

|  | FEED | EN-TRAIN-ER | BOT-TOMS1 | OVER-HEAD1 |
|---|---|---|---|---|
| Temperature (degrees Celsius) | 50 | 50 | 186.6 | 134.5 |
| Pressure (Pascal) | $1.01 \times 10^5$ | $1.01 \times 10^5$ | $1.01 \times 10^5$ | $1.01 \times 10^5$ |
| Vapor Fraction | 0 | 0 | 0 | 0 |
| Mole Flow (mol/h) | 1400.0 | 300.0 | 5900.0 | 8400.0 |
| Mass Flow (kg/h) | 2000.0 | 62.0 | 1014.2 | 1047.8 |
| Volume Flow (cubic meters/h) | 1.8 | 0.1 | 1.1 | 1.0 |
| Mass Flow (kg/h) |  |  |  |  |
| 1,2-dichloropropane | 100 | 0 | 0.0 | 100.0 |
| Epichlorohydrin | 60 | 0 | 0.0 | 60.0 |
| 2-methyl-2-pentenal | 140 | 0 | 0.0 | 140.0 |
| 1,3-dichloro-2-propanol | 540 | 0 | 5.4 | 534.6 |
| 2,2'-oxybis(1-chloropropane) | 1080 | 0 | 1003.2 | 76.8 |
| 1,2,3-trichloropropane | 80 | 0 | 0.2 | 79.8 |
| 1-tetradecene | 0 | 62 | 5.4 | 56.6 |
| Mass Fraction |  |  |  |  |
| 1,2-dichloropropane | 0.05 | 0 | 0 | 0.095 |
| Epichlorohydrin | 0.03 | 0 | 0 | 0.057 |
| 2-methyl-2-pentenal | 0.07 | 0 | 0 | 0.134 |
| 1,3-dichloro-2-propanol | 0.27 | 0 | 0.005 | 0.51 |
| 2,2'-oxybis(1-chloropropane) | 0.54 | 0 | 0.989 | 0.073 |
| 1,2,3-trichloropropane | 0.04 | 0 | 0 | 0.076 |
| 1-tetradecene | 0 | 1 | 0.005 | 0.054 |

TABLE 12

Column 2 process simulation details (1-tetradecene as entrainer)

|  | OVERHEAD1 | OVERHEAD2 | BOTTOMS2 |
|---|---|---|---|
| Temperature (degrees Celsius) | 134.5 | 117.2 | 172.6 |
| Pressure (Pascal) | $1.01 \times 10^5$ | $1.01 \times 10^5$ | $1.01 \times 10^5$ |
| Vapor Fraction | 0 | 0 | 0 |
| Mole Flow (mol/h) | 8383.0 | 3602.0 | 4781.0 |
| Mass Flow (kg/h) | 1047.796 | 392.79 | 655.006 |
| Volume Flow (cubic meters/h) | 1.032 | 0.418 | 0.631 |
| Mass Flow (kg/h) |  |  |  |
| 1,2-dichloropropane | 100.0 | 100.0 | 0.0 |
| Epichlorohydrin | 60.0 | 60.0 | 0.0 |
| 2-methyl-2-pentenal | 140.0 | 140.0 | 0.0 |
| 1,3-dichloro-2-propanol | 534.6 | 13.4 | 521.2 |
| 2,2'-oxybis(1-chloropropane) | 76.8 | 0.0 | 76.8 |
| 1,2,3-trichloropropane | 79.8 | 79.4 | 0.4 |
| 1-tetradecene | 56.6 | 0.0 | 56.6 |
| Mass Fraction |  |  |  |
| 1,2-dichloropropane | 0.095 | 0.255 | 0 |
| Epichlorohydrin | 0.057 | 0.153 | 0 |
| 2-methyl-2-pentenal | 0.134 | 0.356 | 0 |
| 1,3-dichloro-2-propanol | 0.51 | 0.034 | 0.796 |
| 2,2'-oxybis(1-chloropropane) | 0.073 | 0 | 0.117 |
| 1,2,3-trichloropropane | 0.076 | 0.202 | 0.001 |
| 1-tetradecene | 0.054 | 0 | 0.086 |

TABLE 13

Decanter stream details (1-tetradecene as entrainer)

|  | BOTTOMS2 | LIQUID1 | LIQUID2 |
|---|---|---|---|
| Temperature (degrees Celsius) | 172.6 | −25 | −25 |
| Pressure (Pascal) | $1.01 \times 10^5$ | $1.01 \times 10^5$ | $1.01 \times 10^5$ |
| Vapor Fraction | 0 | 0 | 0 |
| Mole Flow (mol/h) | 4781.0 | 4543.0 | 238.0 |
| Mass Flow (kg/h) | 655.034 | 608.928 | 46.106 |
| Volume Flow (cubic meters/h) | 0.632 | 0.447 | 0.056 |
| Mass Flow (kg/h) | | | |
| 1,2-dichloropropane | 0 | 0 | 0 |
| Epichlorohydrin | 0 | 0 | 0 |
| 2-methyl-2-pentenal | 0 | 0 | 0 |
| 1,3-dichloro-2-propanol | 521.235 | 520.25 | 0.985 |
| 2,2'-oxybis(1-chloropropane) | 76.82 | 75.673 | 1.147 |
| 1,2,3-trichloropropane | 0.399 | 0.379 | 0.02 |
| 1-tetradecene | 56.58 | 12.626 | 43.954 |
| Mass Fraction | | | |
| 1,2-dichloropropane | 0 | 0 | 0 |
| Epichlorohydrin | 0 | 0 | 0 |
| 2-methyl-2-pentenal | 0 | 0 | 0 |
| 1,3-dichloro-2-propanol | 0.796 | 0.854 | 0.021 |
| 2,2'-oxybis(1-chloropropane) | 0.117 | 0.124 | 0.025 |
| 1,2,3-trichloropropane | 0.001 | 0.001 | 0 |
| 1-tetradecene | 0.086 | 0.021 | 0.953 |

Example 6

Case IV: 1-Octene as Entrainer

Figure 9:
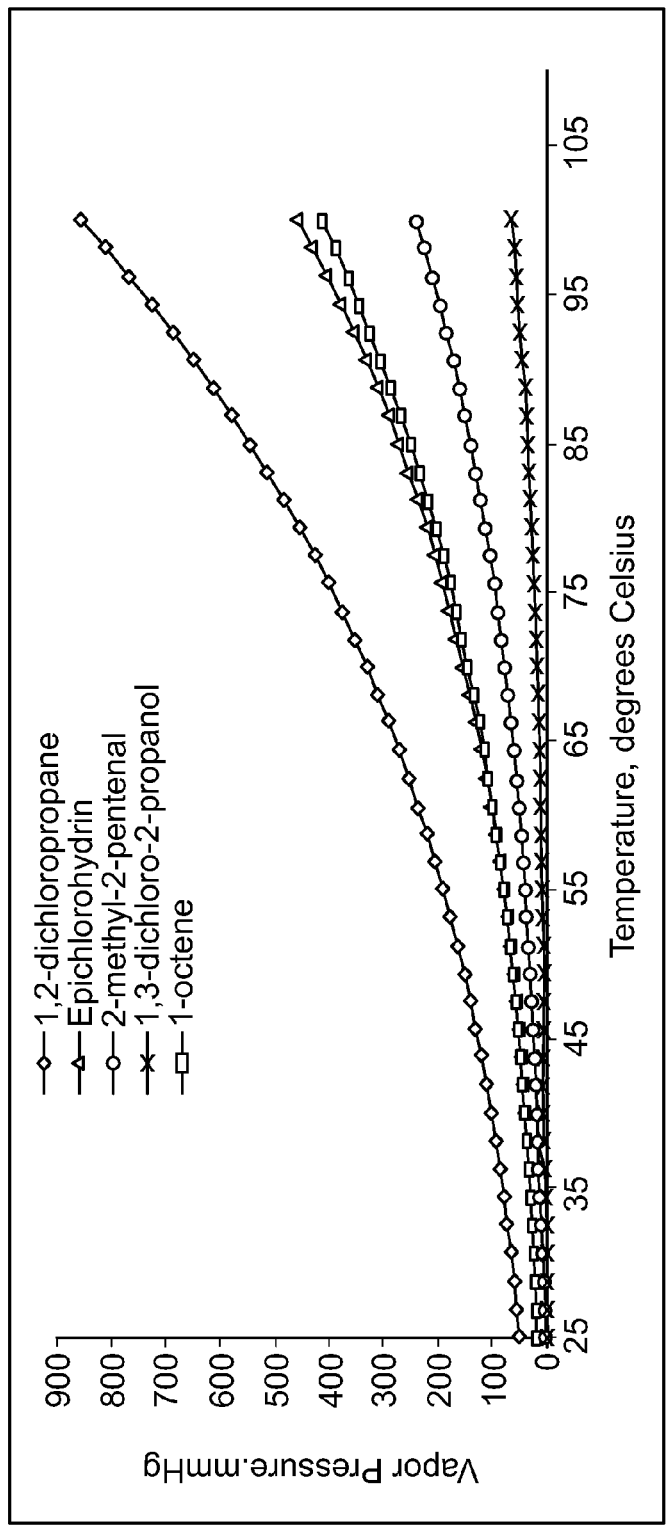
FIG. 9 is a graph of the vapor pressure of 1-octene as compared to 1,2-dichloropropane, epichlorohydrin, 2-methyl-2-pentenal, and 1,3-dichloro-2-propanol.

FIG. 9 shows the vapor pressure of 1-octene as compared to the other species in the system. Unlike the other higher carbon homologues (1-decene, 1-dodecene and 1-tetradecene), 1-octene is an intermediate boiler, thus it would be obtained in the overheads of Column 2 along with 1,2-dichloropropane, epichlorohydrin and 2-methyl-2-pentenal, and would require an additional column for recovery and recycle. In contrast, preferred entrainers would appear in the bottoms of Column 2 along with DCP, which may then be phase-separated and the entrainer recycled back to the azeotropic distillation column. Thus, 1-octene can be used an entrainer, but it is not preferred.

While the invention has been described above according to its preferred embodiments, it can be modified within the spirit and scope of this disclosure. This application is therefore intended to cover any variations, uses, or adaptations of the invention using the general principles disclosed herein. Further, the application is intended to cover such departures from the present disclosure as come within the known or customary practice in the art to which this invention pertains and which fall within the limits of the following claims.

What is claimed is:

1. A process comprising:
    supplying a feed stream and an olefin stream to a first distillation column, the feed stream comprising a target organic compound;
    using the olefin as an entrainer in the first distillation column such that the feed stream is separated into at least a first top stream and a first bottom stream; and
    using a second distillation column to separate the first top stream into at least a second top stream and a second bottom stream.

2. A process according to claim 1, wherein the second bottom stream comprises the target organic compound and the olefin.

3. A process according to claim 1, further comprising separating the second bottom stream in a separator to produce a third bottom stream and the olefin stream, wherein the third bottom stream comprises the target organic compound.

4. A process according to claim 3, further comprising supplying a second olefin stream to the separator.

5. A process according to claim 3, wherein greater than 90 percent of the target organic compound in the feed stream is recovered in the third bottom stream.

6. A process according to claim 2, further comprising reacting the target organic compound in the second bottom stream with the olefin in the second bottom stream.

7. A process according to claim 1, wherein the target organic compound is 1,3-dichloro-2-propanol.

8. A process according to claim 1, wherein the olefin is selected from the group consisting of 1-decene, 1-dodecene, and 1-tetradecene.

9. A process according to claim 1, wherein the feed stream comprises 2,2'-oxybis(1-chloropropane) and 1,3-dichloro-2-propanol.

10. A process according to claim 9, further comprising reacting epichlorohydrin with hydrogen chloride in a reactor to produce the 1,3-dichloro-2-propanol in the feed stream.

11. A process for isolating 1,3-dichloro-2-propanol, the process comprising:
    supplying a feed stream comprising 1,3-dichloro-2-propanol and 2,2'-oxybis(1-chloropropane) to a first distillation column;
    supplying an olefin stream comprising an olefin to the first distillation column;
    using the olefin as an entrainer in the first distillation column, such that the first stream is separated into at least a first top stream and a first bottom stream, wherein the first top stream comprises 1,3-dichloro-2-propanol and the olefin, and wherein the first bottom stream comprises 2,2'-oxybis(1-chloropropane);
    supplying the first top stream to a second distillation column;
    using the second distillation column to separate the first top stream into at least a second top stream and a second bottom stream, wherein the second bottom stream comprises 1,3-dichloro-2-propanol and the olefin;
    separating in a separator the second bottom stream into at least a third bottom stream and a third top stream, wherein the third bottom stream comprises 1,3-dichloro-2-propanol and the third top stream comprises the olefin; and
    returning at least a portion of the third top stream to the first distillation column as the olefin stream.

* * * * *